(12) United States Patent
Thevenin

(10) Patent No.: US 8,128,608 B2
(45) Date of Patent: Mar. 6, 2012

(54) AUTOMATIC PUBIC AREA CLEANING SYSTEM

(76) Inventor: Claude Thevenin, Kingston, NY (US)

( * ) Notice: Subject to any disclaimer, the term of this patent is extended or adjusted under 35 U.S.C. 154(b) by 458 days.

(21) Appl. No.: 12/457,895

(22) Filed: Jun. 24, 2009

(65) Prior Publication Data

US 2010/0004612 A1    Jan. 7, 2010

Related U.S. Application Data

(60) Provisional application No. 61/129,549, filed on Jul. 3, 2008.

(51) Int. Cl.
 *A61F 5/44* (2006.01)
(52) U.S. Cl. ........ 604/347; 604/318; 604/319; 604/327; 604/346; 604/355
(58) Field of Classification Search .................. 604/347, 604/355
See application file for complete search history.

(56) References Cited

U.S. PATENT DOCUMENTS

| | | | |
|---|---|---|---|
| 3,570,488 A | 3/1971 | Diskin et al. | |
| 3,574,239 A | 4/1971 | Sollerud | |
| 4,610,679 A * | 9/1986 | Matsushita | 604/369 |
| 4,655,197 A | 4/1987 | Atkinson | |
| 4,747,166 A | 5/1988 | Kuntz | |
| 5,342,583 A | 8/1994 | Son | |
| 5,681,297 A | 10/1997 | Hashimoto et al. | |
| 6,238,378 B1 | 5/2001 | Perez | |
| 6,352,527 B1 | 3/2002 | Henniges et al. | |
| 6,394,988 B1 * | 5/2002 | Hashimoto | 604/355 |
| 6,443,939 B1 * | 9/2002 | Oki et al. | 604/393 |
| 6,585,709 B2 | 7/2003 | Maimets | |
| 7,135,012 B2 | 11/2006 | Harvie | |
| 7,141,043 B2 | 11/2006 | Harvie | |
| 7,998,125 B2 * | 8/2011 | Weston | 604/317 |
| 2002/0022811 A1 * | 2/2002 | Kim | 604/347 |
| 2002/0143318 A1 | 10/2002 | Flinchbaugh | |
| 2005/0187528 A1 | 8/2005 | Berg | |
| 2007/0293830 A1 | 12/2007 | Martin | |

* cited by examiner

*Primary Examiner* — Loan Thanh
*Assistant Examiner* — Peter S Vasat
(74) *Attorney, Agent, or Firm* — Richard C. Litman

(57) ABSTRACT

The automatic pubic area cleansing system includes a ventilated diaper and a removable insert pad. At least one sensor is disposed in the system. The sensors are connected to a control unit that activates a ventilating and evacuating system when moisture is detected in the diaper. A massage head is disposed in a rear portion of the pad and can provide stimulation to the coccyx area of the patient to prevent the formation of a decubitus ulcer in the region.

20 Claims, 8 Drawing Sheets

AUTOMATIC PUBIC AREA CLEANING SYSTEM

CROSS-REFERENCE TO RELATED APPLICATION

This application claims the benefit of U.S. Provisional Patent Application Ser. No. 61/129,549, filed Jul. 3, 2008.

BACKGROUND OF THE INVENTION

1. Field of the Invention

The present invention relates to the general art of health care, and particularly to an automatic pubic area cleansing system for monitoring, cleansing and massaging incontinent patients.

2. Description of the Related Art

One of the problems in the care of incontinent patients is the frequency of leakage in the use of diapers. It has been found that the capillary forces in the absorption body in the diaper cannot counteract gravitation forces to any great extent, and, thus, there are often leakages, particularly when the patient is lying on his side. Incontinence diapers provided with elastic bands currently in the market today have an extension of the band solely in the crotch portion, and thus optimum flexibility in the whole diaper is not achieved, which means that the diapers must be manufactured in several different sizes. In spite of this, they often leak when in use.

Still further, if waste, such as urine, is not removed from contact with the patient, diseases, rashes and the like can result. An indwelling catheter has been used to alleviate some of the aforementioned problems. However, frequent catheterization may induce urinary tract infection, which is very common in hospitals, nursing homes, and the like. Also, in immobile patients there exists the problem of decubitus ulcers (also referred to as pressure ulcers, pressure sores, or bedsores) developing on a patient's skin. These ulcers are a pervasive problem in the health care field, with high cost both in terms of individual human suffering and the financial cost to society.

The incidence of decubitus ulcers in hospitalized patients and in the nursing home patient is high. A decubitus ulcer is a localized cellular necrosis that tends to develop when soft tissue is compressed between a bony prominence and a firm surface for prolonged periods of time. External pressure exerts its influence by occluding blood flow, leading to ischemic injury. With the interruption of blood flow and hence oxygen supply, a sequence of intracellular events occurs that proceeds to an irreversible stage if the blood flow is not restored.

It is generally accepted that the basic treatment of decubitus ulcers is prevention. There have been attempts at prevention, such as the use of foam padding, sheepskin mattresses having an egg-crate surface, silicon gel pads, sponge rubber and air mattresses, special padding for wheelchairs, and the like. However, these preventive measures still do not provide the patient with a long-term, relaxing, comfortable experience.

Thus, an automatic pubic area cleansing system solving the aforementioned problems is desired.

SUMMARY OF THE INVENTION

The automatic pubic area cleansing system includes a ventilated diaper and a removable insert pad. At least one sensor is disposed in the system. The sensors are connected to a control unit that activates a ventilating and evacuating system when moisture is detected in the diaper. A massage head is disposed in a rear portion of the pad and can provide stimulation to the coccyx area of the patient, thereby restoring blood circulation in order to avoid any ischemic injury or cell death (necrosis), and to prevent the formation of a decubitus in the region.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
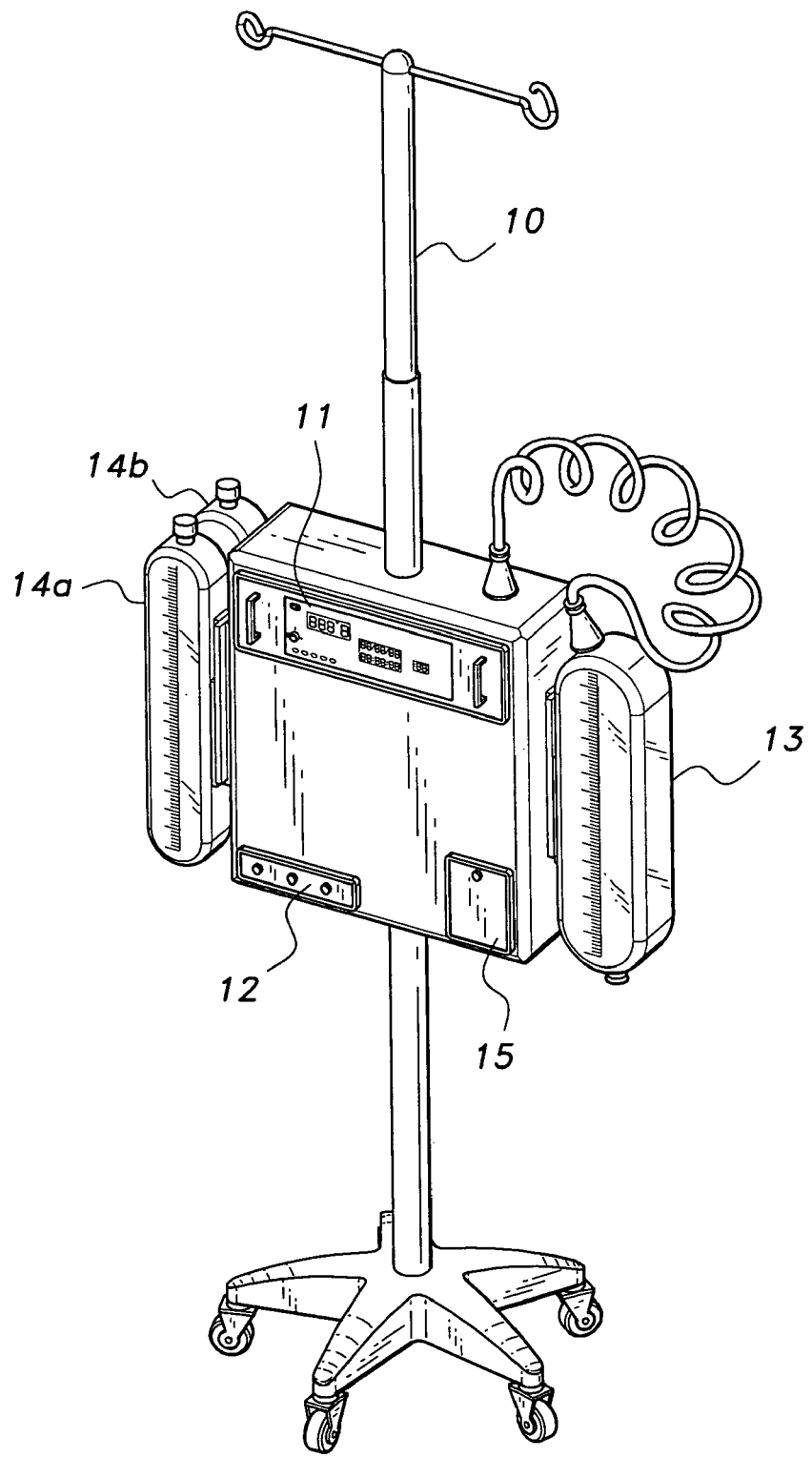
FIG. 1A is a perspective view of a control unit of an automatic pubic area cleansing system according to the present invention.
Figure 1B:
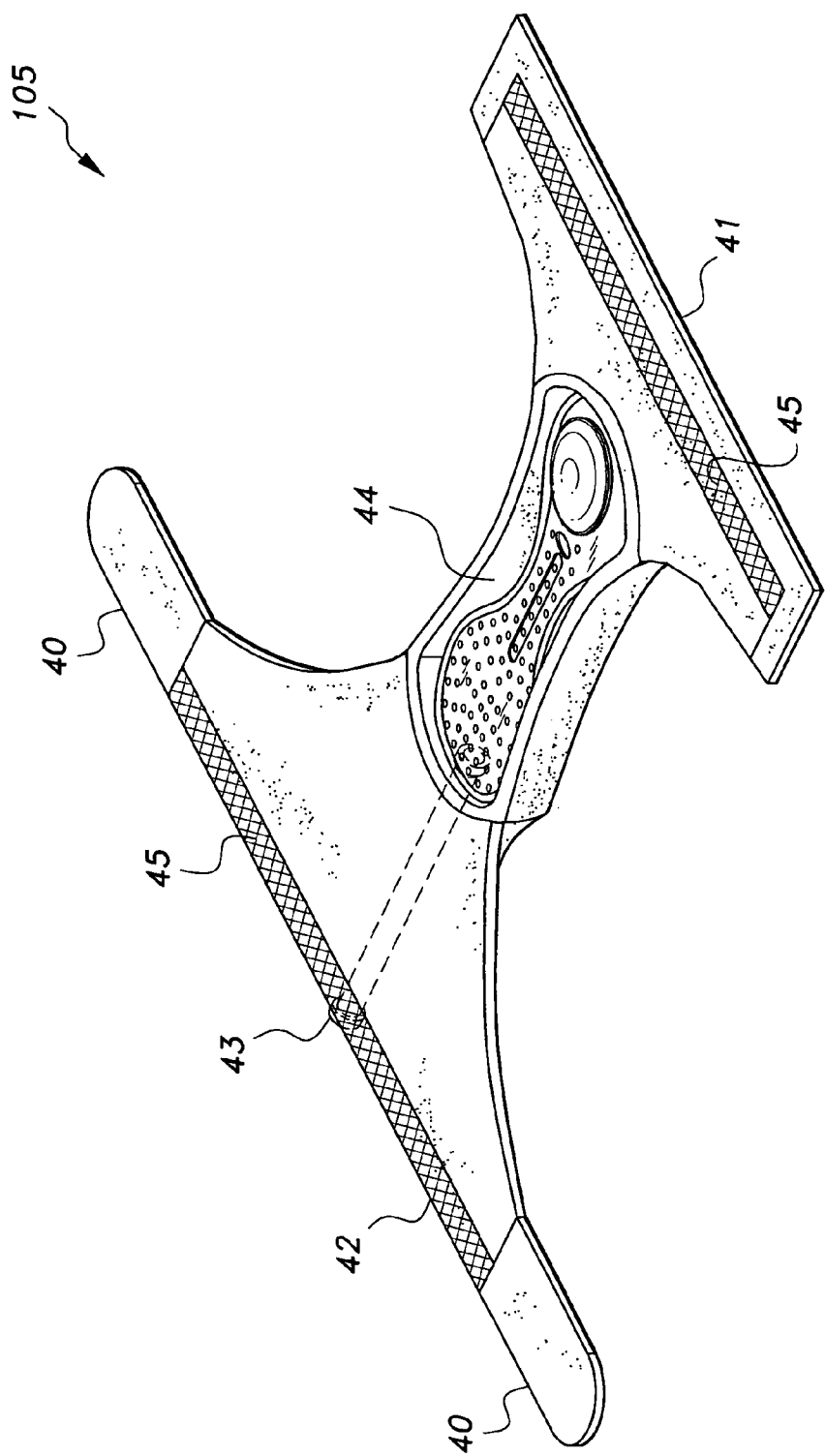
FIG. 1B is a perspective view of a diaper element of an automatic pubic area cleansing system according to the present invention.

As shown in FIGS. 1A-1D and 3, the present invention relates to an automatic pubic area cleansing system 5 that includes a diaper 105 and insert pad 110. Diaper 105 with pad 110 envelops a patient's pubic, crotch and buttocks areas. A front panel 42 covers a front pubic portion of the patient. Belt wings 40 extend from the front panel and may comprise, for example, hook and loop fasteners to secure diaper 105 in place on the patient. A rear panel 41 covers the buttocks portion of the patient. Both front panel 42 and rear panel 41 include an elongate air-permeable strip of material 45 that lets air evacuate away from the internal portions of diaper 105. Belt wings 40 are flexible and can wrap around to the rear panel 41, which may have a complementary surface to engage fasteners on the belt wings 40. A hollowed-out crotch section 44 connects the front panel 42 to the rear panel 41 and provides an adhesive-lined recess for insertion of the pad 110. As shown in FIG. 1B, a fluid conduit extends through the diaper 105 from the recess defined by hollowed-out crotch section 44 to a periphery of the diaper 105, terminating in a connector plug 43.

Urine detection sensor 155a is mounted inside the pad 110 and sends "urine present" status information to a control unit 25 upon sensing urine in the diaper 105 by any of a number of well-known methods. The control unit 25 can then activate a water pump 20 to wash the urine away from diaper 105 and diaper pad 110. In this manner, diaper rash in the patient may be avoided, since diaper rash is caused by contact irritation, with local skin infection due to overgrowth of the stratum corneum or outermost layer of the skin in the pubic area. Although wetness alone macerates the skin, softening the stratum corneum greatly increases susceptibility and friction injury.

Urine has an additional impact on skin irritants, causing itching and resulting in erythema. In this case, the skin is necessarily more vulnerable to secondary infections by bacteria and fungi at the perineal and inguinal areas. *Candida albicans* may develop also, but is more likely in children with symptomatic diaper rash. *Candida* is the most common opportunistic invader in diaper areas. Once the skin is compromised, secondary infection by *Candida albicans* is common. Between 40% and 75% of diaper rashes that last for more than three days are colonized with *Candida albicans*.

Due to the aforementioned problems, the automatic pubic area cleansing system 5 employs an air delivery system comprising air pump 23 to dry the diaper 105 and pad 110, and also to dry the patient's skin in contact with the diaper 105 and pad 110. This drying cycle is generally initiated by control unit 25 after the washing cycle has completed.

Figure 4:
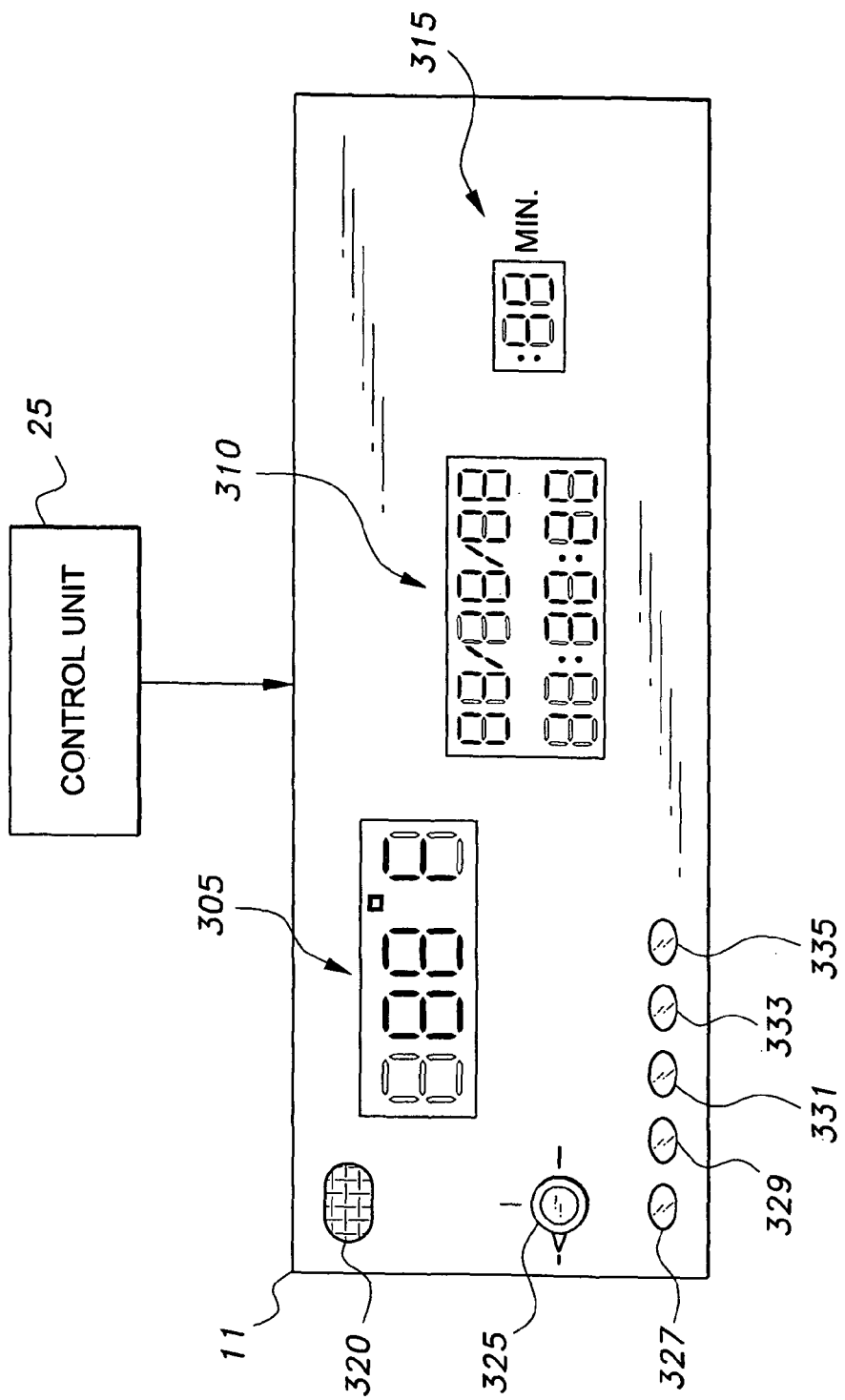
FIG. 4 is a front view of an exemplary control unit and display panel for an automatic pubic area cleansing system according to the present invention.

In addition, a stool sensor 155b is mounted inside the pad 110. The stool sensor 155b sends "stool present" status information to the control unit 25 upon sensing stool in the diaper 105. To warn a caregiver of a soiled diaper 105, the control unit 25, as shown in FIG. 4, has a "stool present" indicator 335 disposed on display panel 11. The stool present indicator 335 alerts the caregiver whenever the stool sensor 155b detects stool present. The caregiver then removes the diaper 105 and pad 110, cleans the patient, and installs a clean diaper 105 and pad 110.

Power supply 26 (preferably a battery mounted in a compartment 15 situated in a housing of the control unit 25) supplies electrical power to the control unit 25 and other components of system 5 that require electrical power.

The control unit 25 is associated with the diaper 105 and pad 110 and may be disposed on a transportable stand 10 that can be conveniently positioned next to the patient. Control unit 25 may comprise a processor, microprocessor, or the like, that can process information sent by the sensors, such as urine and stool sensors 155a and 155b. Control unit 25 is in operable communication with a water pump 20 and can activate the water pump 20 when urine is detected at urine sensor 155a. Timing circuitry of control unit 25 can de-activate water pump 20 after a predetermined time of water pump operation.

An air pump 23 is in operable communication with the control unit 25, which activates the air pump 23 when the water pump 20 is de-activated. Timer circuitry in the control unit 25 de-activates the air pump 23 after a predetermined time of air pump operation. The air pump 23 and water pump 20 may be located in the housing of control unit 25.

As shown in FIGS. 1A-1C and 1E, a triple lumen tube 600 has a first end 31 connected to the diaper pad 110 through a connector plug 43 disposed in a pocket-like opening in diaper 105, and a second end 30 connected to control unit 25 at connection port 12. The tube 600 comprises a water supply line, an air supply line, and a wastewater return line for hygienic service of the diaper pad 110. The triple lumen tube 600 is broken out into a "water in" lumen, i.e., water supply line 32, a "water out" lumen, i.e., waste water return line 33, and an "air in lumen", i.e., air supply line 34.

Figure 3:
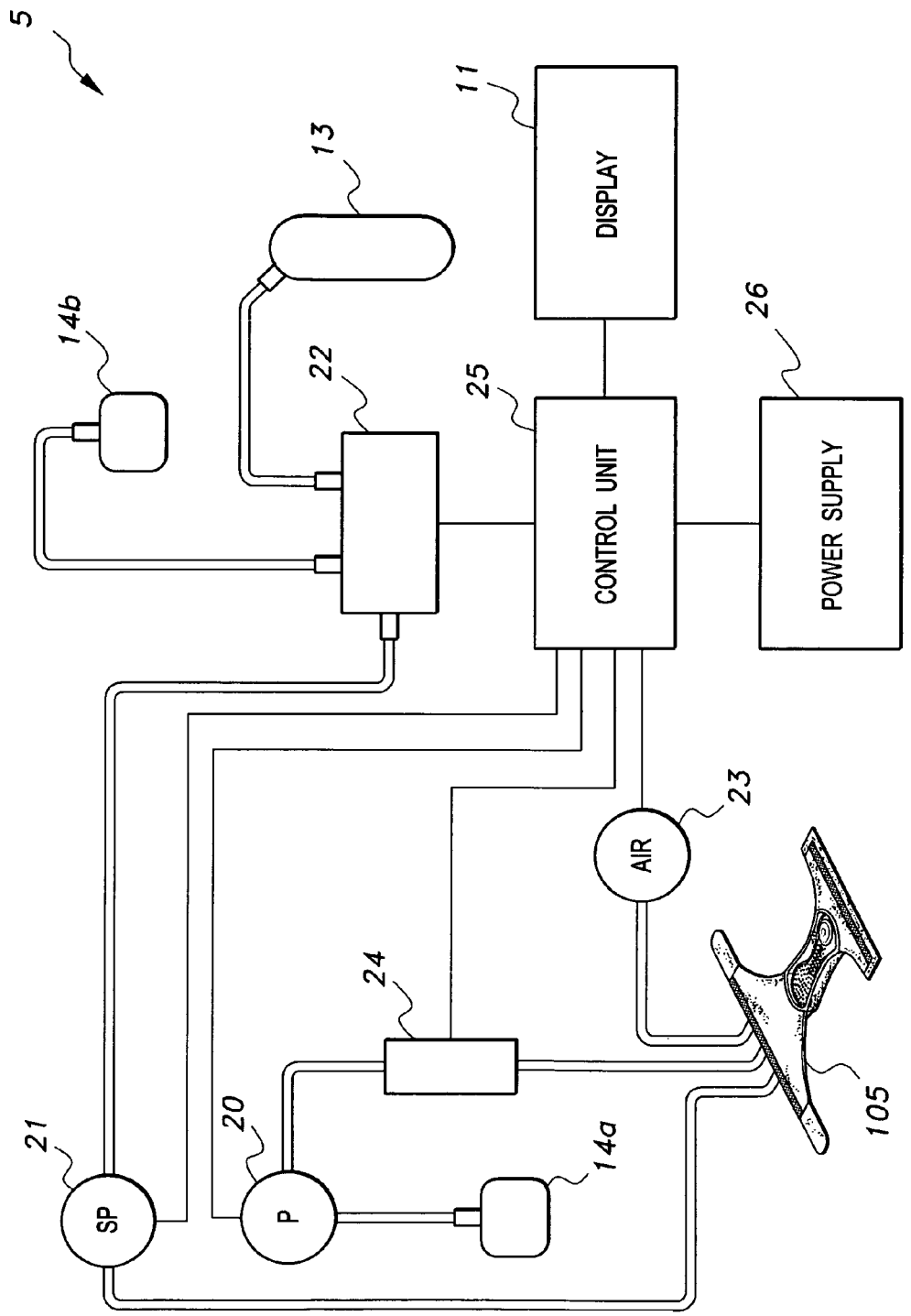
FIG. 3 is a block diagram of an automatic pubic area cleansing system according to the present invention.

The water supply line 32 of triple lumen tube 600 connects the water pump 20 to the diaper pad 110 via diaper connector plug 43. As shown in FIG. 3, clean (preferably distilled) water supply container 14a is connected to an inlet of heater 24. An outlet of heater 24 is connected to an inlet of water pump 20. The output of water pump 20 feeds clean, preferably distilled water to the water inlet portion of the diaper pad 110. The heater 24 may be thermostatically controlled independently or by control unit 25 and is designed to heat water supplied to diaper pad 110 via water pump 20 to a comfortable temperature for the patient.

Figure 1C:
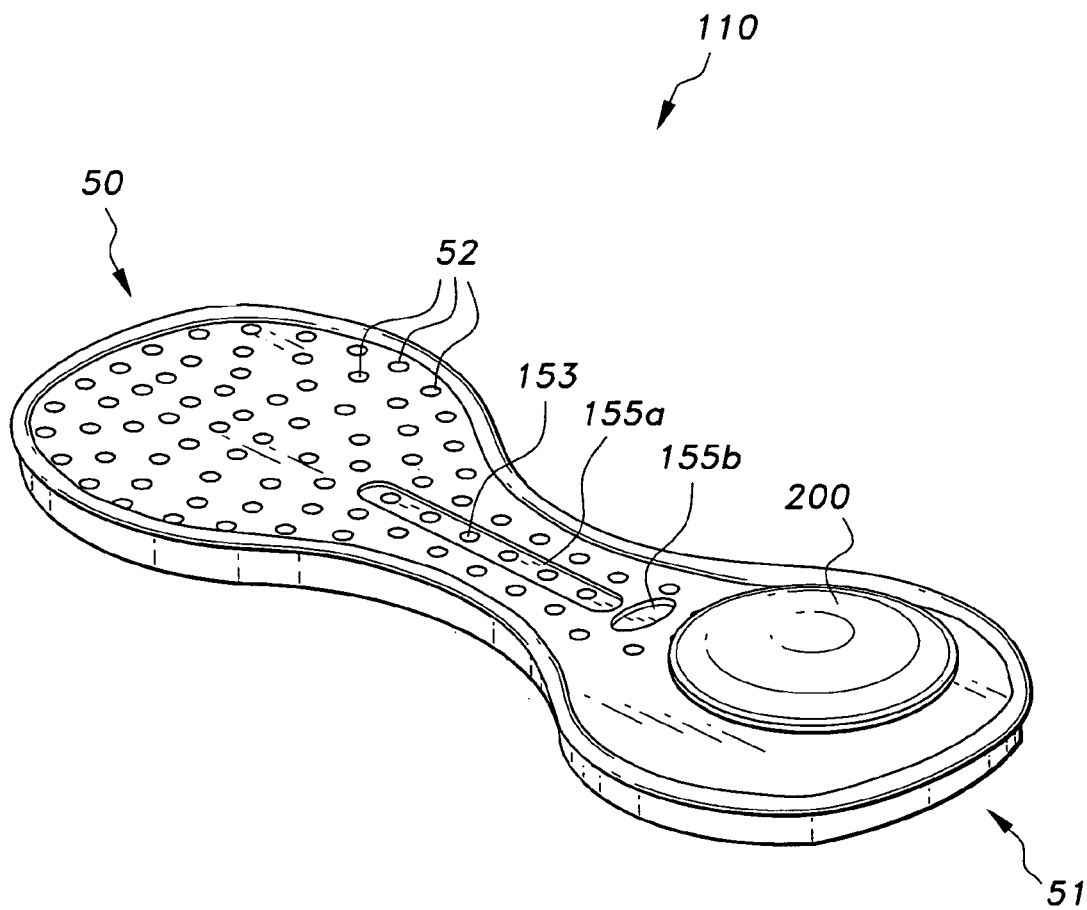
FIG. 1C is a top perspective view of a diaper pad of an automatic pubic area cleansing system according to the present invention.
Figure 1D:
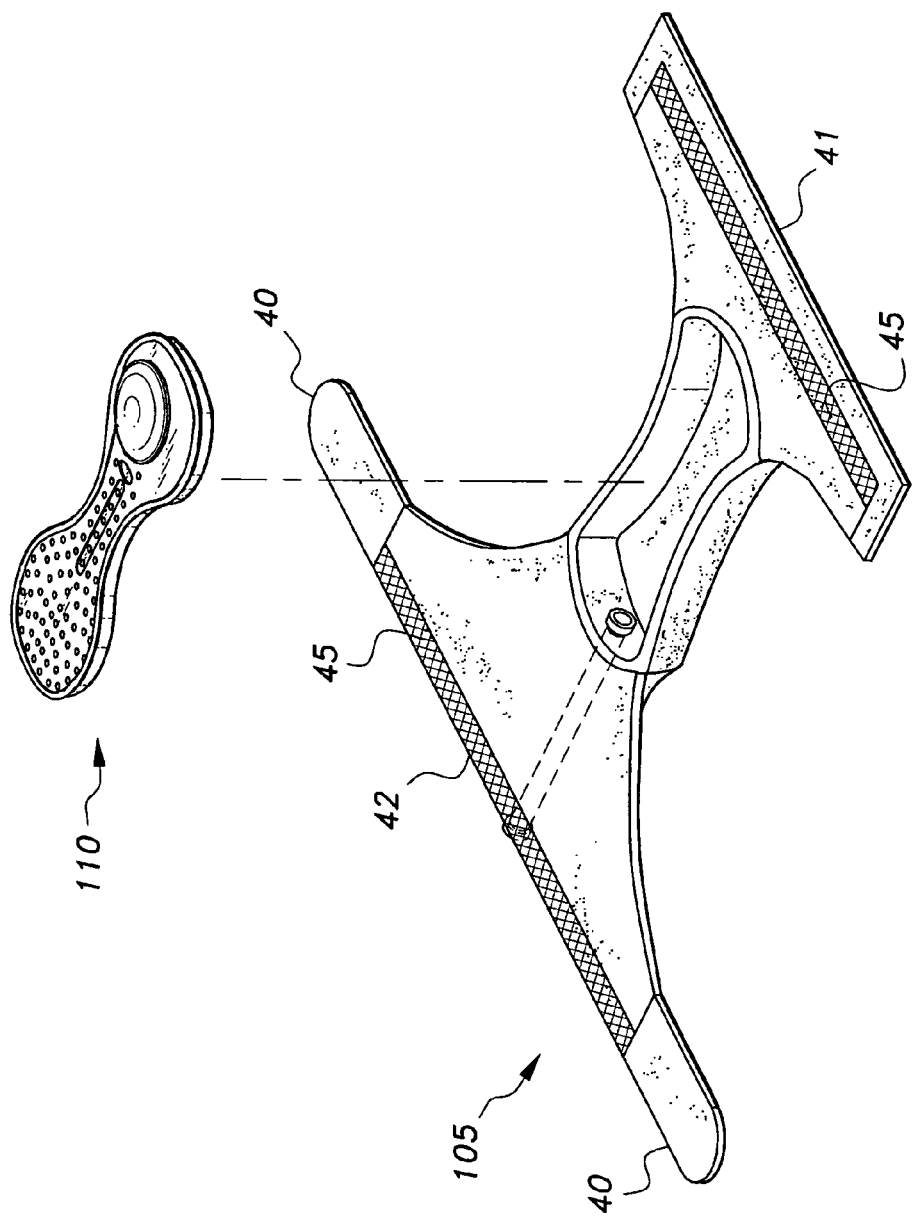
FIG. 1D is an exploded perspective view of a pad and diaper assembly of an automatic pubic area cleansing system according to the present invention.
Figure 1E:
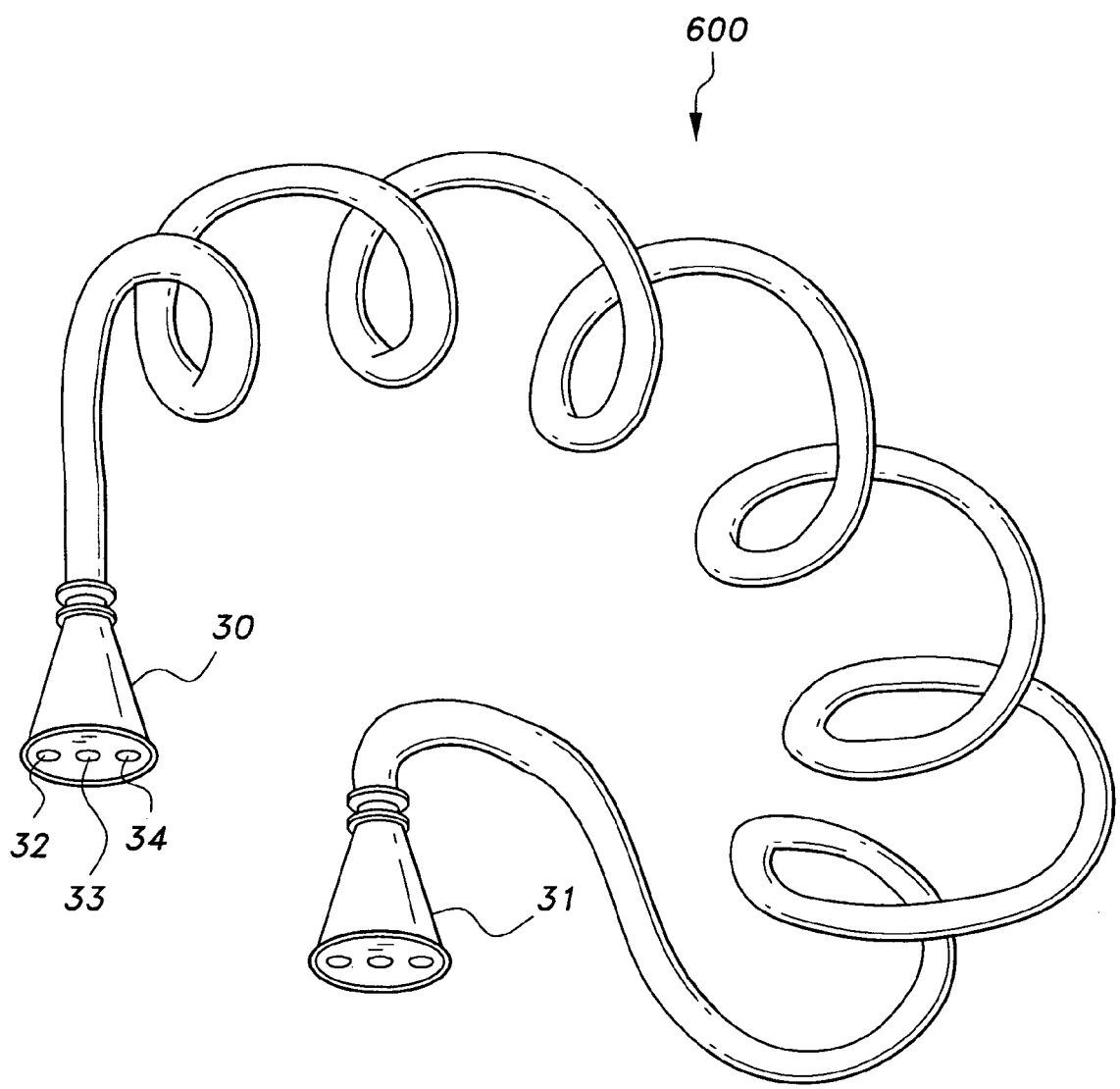
FIG. 1E is a perspective view of a triple lumen tube of an automatic pubic area cleansing system according to the present invention.

The diaper pad 110 is, as shown in FIG. 1C, an elongate flexible member having a flared out arcuate front end 50 and a flared out arcuate rear end 51. The body of the diaper pad 110 is water permeable to accommodate water flow distributed by water pump 20. Outside surfaces of the diaper pad 110 are impermeable to water, except for portions of the upper outside surface, which have a plurality of water jets 52. The urine sensor 155a is disposed in a mid portion of the upper outside surface of the diaper pad 110. Urine inlet holes 153 are disposed above the urine sensor 155a to allow urine to drip onto the urine sensor 155a for activation. The stool sensor 155b is disposed proximate the rear portion of the upper outside surface of the diaper pad 110.

The air supply line 34 of triple lumen 600 connects air pump 23 to an air inlet port of the diaper pad 110. The air supplied to diaper pad 110 can dry the diaper 105 and diaper pad 110 after a cleansing operation without a caregiver having to remove the diaper 105 and pad 110 from the patient.

The water return line 33 of triple lumen 600 is connected to a water outlet port of diaper pad 110. A waste water container 14b is connected to a first outlet of pump switch 22. A urine bag 13 is connected to a second outlet of pump switch 22. The water return line 33 is connected to an inlet of suction pump 21. An outlet of suction pump 21 is connected to an inlet of pump switch 22. Based on whether the urine sensor 155a detects urine in diaper pad 110, the control unit 25 commands a valve in pump switch 22 to open the second pump switch outlet for collecting urine in urine bag 13 for later disposal. Otherwise, the control unit 25 commands the valve in pump switch 22 to open the first pump switch outlet for collecting waste water in waste water container 14b for later disposal.

A massage head 200 is disposed in the rear arcuate portion of the pad and, responsive to actuation by control unit 25, can provide stimulation to the coccyx area of the patient. The massage head 200 is air actuated and receives moderate pressure air delivered by air pump 23 during the drying cycle. A plurality of hollow balls 57a having air perforations 260 is disposed in a spiraling arrangement inside spiro-coiled massage head air tube 99 within the circular periphery of massage head base 204.

Figure 2A:
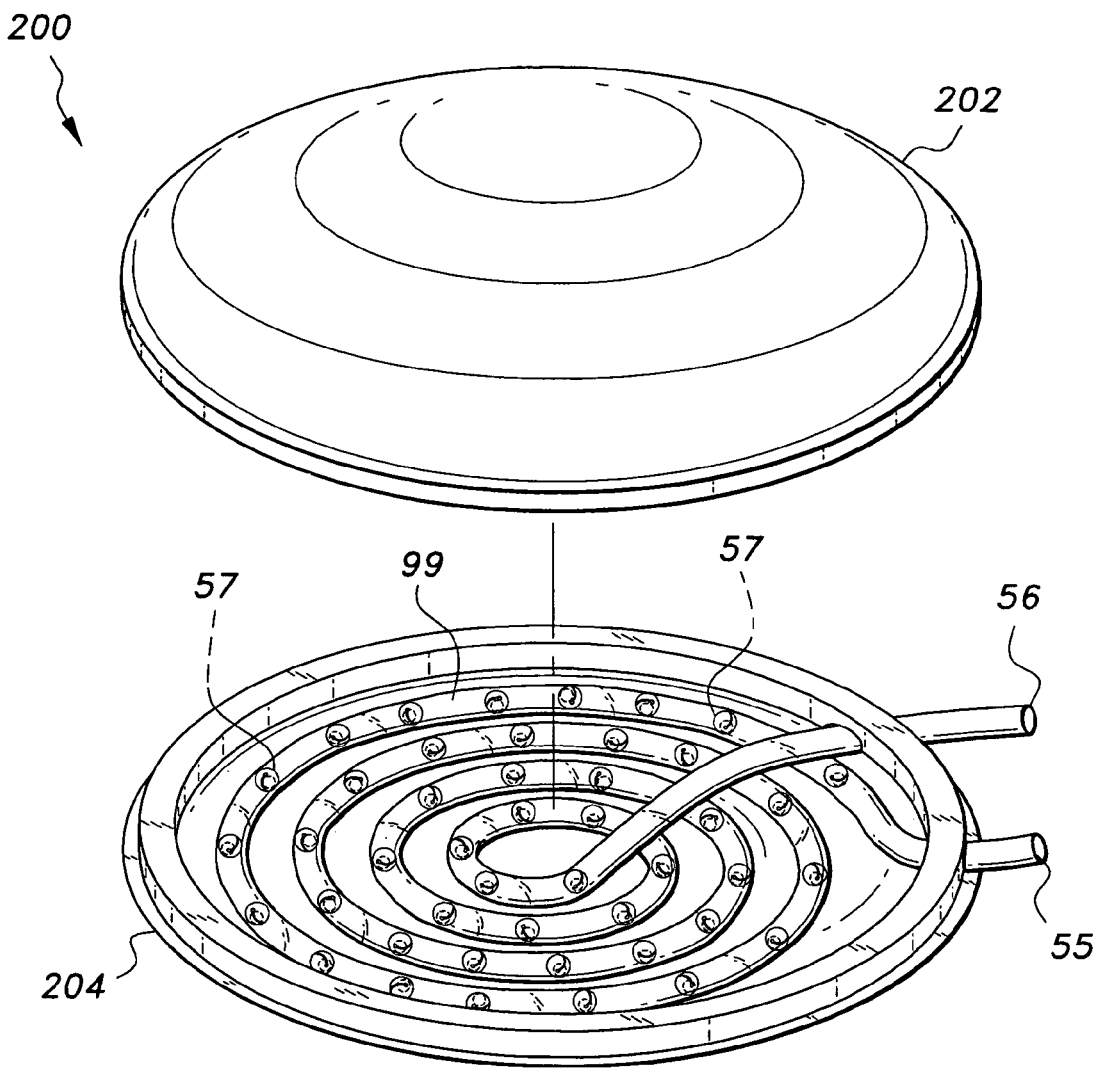
FIG. 2A is an exploded perspective view of a massage head in an automatic pubic area cleansing system according to the present invention.
Figure 2B:
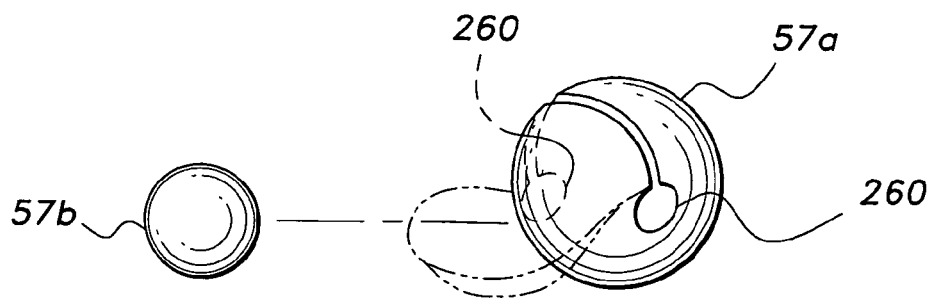
FIG. 2B is an exploded perspective view of massage head metallic balls for an automatic pubic area cleansing system according to the present invention.

Referring now to FIGS. 2A-2B, a solid ball of smaller dimension 57b is disposed in each of the hollow balls 57a. The smaller balls 57b are small enough to rattle inside large balls 57a when perturbed by an outside force, such as air being delivered to the massage head air tube 99 by air pump 23 via air intake 55. The massage head air tube 99 provides moderate air pressure for flow through the perforated balls 57a to rattle small balls 57b. The rattling action of the air-perturbed small balls 57b inside the large balls 57a is sufficient to cause wave-like, vibratory massaging action through cover 202 of the massage head 200. The cover 202 is a pliant material that comes in contact with the wearer's coccyx to deliver the massaging action of the massage head 200 to the patient. Air is exhausted from the massage head 200 via air outlet 56. The air circulates through the rest of the diaper pad 110 for drying action of the pad 110, diaper 105, and wearer as air escapes through the water jets 52.

Initially, when urine is detected at sensor 155a, the control unit 25 receives the positive urine present status information from sensor 155a and then activates suction pump 21 to suction urine from diaper pad 110 incident to the crotch area of the patient. The suctioned urine is delivered to the urine bag 13 via suction action of the suction pump 21, the control unit 25 activating the second outlet of the pump switch 22. When the control unit detects that no more liquid is being suctioned by suction pump 21, the control unit 25 commands the suction pump off and subsequently commands the water pump 20 on. Clean, preferably distilled water from container 14a is heated by heater 24 and travels through water pump 20 as the pump 20 injects warm water to the wearer's pubic area via the water jets for a predetermined washing time to wash the area from urine. The control unit 25 then commands the suction pump 21 back on to suction waste water out of the pad 110.

Since the urine detection status reported back to the control unit 25 should be negative at this time, the control unit 25 commands valve at pump switch 22 to activate the first outlet of the pump switch to allow the suctioned waste water to flow into container 14b. Preferably, the control unit 25 may be programmed to perform the wash and suction cycle two times.

Subsequent to the wash and suction cycles, the control unit 25 deactivates the suction pump 21 and the water pump 20, and activates the blower (air pump 23), which then circulates warm, temperature-regulated air through areas of pad 110 that have previously been washed. The circulation of air through the pad 110 begins at air intake 55, leading to the massage head air tube 99. Thus, the aforementioned massaging action is delivered to the patient by massage head 200 while the air, via airflow out of massage head air outlet 56 and through jets 52, is drying the diaper 105 and pad 110.

Vibratory massaging action delivered by massage head 200 is expected to promote blood circulation in the contact area of the wearer (patient), thus avoiding dead muscle, skin break and decubitus formation in the massaged area of the patient. The control unit 25 may command the air pumping cycle to continue for a predetermined time, after which the control unit 25 commands the air pump 23 to stop. Preferably, under control of control unit 25, the air circulation/massage cycle is repeated every thirty minutes until urine is again detected by urine sensor 155a, at which time the wash cycle is initiated.

When the stool sensor 155b sends "stool present" status information to the control unit 25 upon sensing stool in the diaper 105, the control unit 25 activates a "stool present" indicator 335 disposed in control unit display device 11, as shown in FIG. 4, (display device 11 may be a display panel, screen, or the like), to warn the caregiver of the soiled diaper 105. The caregiver then responds by stopping the system 5 via mode selector 325, removing diaper 105, separating the pad 110 therefrom, washing the pad 110, and dressing the patient with a washed, reused pad 110 in a new diaper 105.

As shown in FIG. 4, control unit display device 11 features a temperature display 305, a clock display 310, a timer display 315, an alarm speaker or speaker icon 320, a mode selector/indicator 325, a low battery indicator 327, an empty bottle indicator 329, a waste bag full indicator 331, a tube obstruction indicator 333, and the "stool present" indicator 335.

It is to be understood that the present invention is not limited to the embodiment described above, but encompasses any and all embodiments within the scope of the following claims.

I claim:

1. An automatic pubic area cleansing system, comprising:
a multiple lumen air and liquid transport tube;
a diaper having a hollowed-out crotch section defining a recess, the diaper having a periphery;
a fluid conduit extending from the periphery of the diaper to the recess, the multiple lumen tube being connected to the fluid conduit;
a diaper pad removably inserted into the recess in the diaper, the diaper pad being attachable to the fluid conduit;
a control unit connected to the multiple lumen tube;
a urine sensor mounted in the diaper pad, the urine sensor communicating a signal to the control unit of the presence of urine on the diaper pad;
means for distributing air to the diaper pad though a lumen of the multiple lumen tube responsive to commands from the control unit;
means for distributing clean water to the diaper pad via a first liquid transport tube responsive to commands from the control unit based on the presence of urine on the diaper pad being detected by the urine sensor, the diaper pad having a plurality of holes defined therein distributing the clean water to the diaper pad in a jet stream, the jet stream washing the diaper pad, diaper, and a wearer of the diaper and pad;
means for suctioning waste liquid from the diaper pad responsive to commands from the control unit;
means for collecting the suctioned waste liquid for later disposal; and
an air-driven massage head disposed in the diaper pad, the air-driven massage head being driven by the means for distributing air to the diaper pad, the distributed air also traveling through the plurality of holes in the diaper pad, the plurality of holes forming an air stream, the air stream drying the wearer, pad and diaper;
wherein the wearer of the diaper and diaper pad is kept clean and dry, a portion of the wearer's body being periodically massaged by contact of the massage head with said portion of the wearer's body.

2. The automatic pubic area cleansing system according to claim 1, wherein the massage head comprises:
a spiro-coiled air tube disposed in the massage head;
a plurality of hollow balls having air perforations disposed inside the spiro-coiled air tube of the massage head;
a solid ball of smaller dimension being disposed in each of the hollow balls, the smaller solid balls being small enough to rattle inside the larger, hollow balls when perturbed by air being delivered to the massage head air tube, thereby delivering wave-like, vibratory massaging action through the massage head.

3. The automatic pubic area cleansing system according to claim 2, wherein the massage head further comprises a cover made of a pliant material, the cover being adapted for coming in contact with a wearer's body to transmit the massaging action of the massage head to the wearer.

4. The automatic pubic area cleansing system according to claim 1, wherein the diaper comprises:
a front panel adapted for covering a front pubic portion of the patient;
belt wings extending from the front panel, the belt wings including fasteners adapted for securing the diaper in place on the wearer; and
a rear panel adapted for covering the buttocks portion of the wearer, both the front panel and the rear panel including an elongate air-permeable strip of material allowing air to evacuate away from internal portions of the diaper, the belt wings being flexible, wrapping around said rear panel, said rear panel having a complementary surface to engage fasteners on the belt wings.

5. The automatic pubic area cleansing system according to claim 1, wherein the diaper recess includes an adhesive liner, thereby facilitating placement of the diaper pad into the recess in said diaper.

6. The automatic pubic area cleansing system according to claim 1, further comprising means for sequencing said waste liquid suctioning means after said clean water distributing means.

7. The automatic pubic area cleansing system according to claim 6, further comprising means for sequencing said drying air distribution means after said waste liquid suctioning means.

8. The automatic pubic area cleansing system according to claim 1, further comprising a stool sensor mounted inside the pad, the stool sensor sending a "stool present" status message to said control unit upon sensing stool in said diaper, the status message notifying a caregiver that manual cleaning of the wearer is required.

9. The automatic pubic area cleansing system according to claim 1, further comprising a thermostatically controlled heating unit heating the clean water to a comfortable temperature for the wearer.

10. The automatic pubic area cleansing system according to claim 1, further comprising a transportable stand, said control unit being disposed thereon for convenient positioning next to a wearer of the diaper.

11. An automatic pubic area cleansing system, comprising:
a multiple lumen air and liquid transport tube;
a diaper having a hollowed-out crotch section defining a recess, the diaper having a periphery;
a fluid conduit extending from the periphery of the diaper to the recess, the multiple lumen tube being connected to the fluid conduit;
a diaper pad removably inserted into the recess in the diaper, the diaper pad being attachable to the fluid conduit;
a control unit connected to the multiple lumen tube;
a urine sensor mounted in the diaper pad, the urine sensor communicating a signal to the control unit of the presence of urine on the diaper pad;
an air pump distributing air to the diaper pad though a lumen of the multiple lumen tube, said air pump being responsive to commands from the control unit;
a water pump distributing clean water to the diaper pad via a first liquid transport tube, said water pump being responsive to commands from the control unit based on the presence of urine on the diaper pad being detected by the urine sensor, the diaper pad having a plurality of holes defined therein distributing the clean water pumped by said water pump to the diaper pad in a jet stream, the jet stream washing the diaper pad, diaper, and a wearer of the diaper and pad;
a vacuum pump suctioning waste liquid from the diaper pad, said vacuum pump being responsive to commands from the control unit;
a waste liquid bag collecting the suctioned waste liquid for later disposal; and
an air-driven massage head disposed in the diaper pad, the air-driven massage head being driven by the means for distributing air to the diaper pad, the distributed air also traveling through the plurality of holes in the diaper pad, the plurality of holes forming an air stream, the air stream drying the wearer, pad and diaper;

wherein the wearer of the diaper and diaper pad is kept clean and dry, a portion of the wearer's body being periodically massaged by contact of the massage head with said portion of the wearer's body.

12. The automatic pubic area cleansing system according to claim 11, further comprising a thermostatically controlled heating unit connected in-line between the clean water pump and the diaper, the heating unit heating the clean water to a comfortable temperature for the wearer of the diaper.

13. The automatic pubic area cleansing system according to claim 11, further comprising:
a urine bag; and
a valve having an inlet port and two outlet ports, output of said suction pump being connected to the inlet port, said waste liquid bag being connected to a first of said two outlet ports, said urine bag being connected to a second of said two outlet ports, said control unit commanding said valve to divert waste flow to said urine bag when said urine sensor detects urine in said diaper and to divert waste flow to said waste liquid bag when urine is no longer detected by said urine sensor.

14. The automatic pubic area cleansing system according to claim 11, further comprising a stool sensor mounted inside the pad, the stool sensor sending a "stool present" status message to said control unit upon sensing stool in said diaper, the status message notifying a caregiver that manual cleaning of the wearer is required.

15. The automatic pubic area cleansing system according to claim 11, wherein the control unit further comprises a display panel displaying clean water temperature and control unit cycle timing.

16. The automatic pubic area cleansing system according to claim 11, wherein the control unit further comprises a mode selector switch selectively engaging washing, suctioning and drying modes of the system.

17. The automatic pubic area cleansing system according to claim 11, wherein the control unit further comprises:
a clock display;
an alarm speaker;
a low battery indicator;
an empty bottle indicator;
a waste bag full indicator;
a tube obstruction indicator; and
a stool present indicator.

18. An automatic pubic area cleansing system, comprising:
a diaper having a hollowed-out crotch section defining a recess, the diaper having a periphery;
a fluid conduit extending from the periphery of the diaper to the recess, the fluid conduit accepting delivery of clean water and dry air to the diaper, said fluid conduit also returning waste fluid from the diaper;
a diaper pad removably inserted into the recess in the diaper, the diaper pad being attachable to the fluid conduit;
a urine sensor mounted in the diaper pad, the urine sensor detecting the presence of urine on the diaper pad;
the diaper pad having a plurality of holes defined therein distributing the clean water to the diaper pad in a jet stream, the jet stream washing the diaper pad, diaper, and a wearer of the diaper and pad; and
an air-driven massage head disposed in the diaper pad, the air-driven massage head being driven by the dry air delivered to the diaper pad, the dry air also traveling through the plurality of holes in the diaper pad, the plurality of holes forming an air stream, the air stream drying the wearer, pad and diaper;

wherein the wearer of the diaper and diaper pad is kept clean and dry, a portion of the wearer's body being periodically massaged by contact of the massage head with said portion of the wearer's body.

19. The automatic pubic area cleansing system according to claim 18, further comprising:

means for controlling air and clean water delivery, waste water return to/from the diaper;

means for distributing air to the diaper pad responsive to commands from said controlling means;

means for distributing clean water to the diaper pad responsive to commands from said controlling means based on the presence of urine on the diaper pad being detected by the urine sensor, the diaper pad having a plurality of holes defined therein distributing the clean water to the diaper pad in a jet stream, the jet stream washing the diaper pad, diaper, and a wearer of the diaper and pad;

means for suctioning waste liquid from the diaper pad responsive to commands from said controlling means; and means for collecting the suctioned waste liquid for later disposal.

20. The automatic pubic area cleansing system according to claim 18, wherein the massage head comprises:

a spiro-coiled air tube disposed in the massage head;

a plurality of hollow balls having air perforations disposed inside the spiro-coiled air tube of the massage head; and a solid ball of smaller dimension being disposed in each of the hollow balls, the smaller solid balls being small enough to rattle inside the larger, hollow balls when perturbed by air being delivered to the massage head air tube, thereby delivering wave-like, vibratory massaging action through the massage head.

* * * * *